(12) United States Patent
Kroening

(10) Patent No.: US 8,794,242 B1
(45) Date of Patent: Aug. 5, 2014

(54) INFANT EYE GUARD APPARATUS

(76) Inventor: Christine Kroening, Aldie, VA (US)

( * ) Notice: Subject to any disclaimer, the term of this patent is extended or adjusted under 35 U.S.C. 154(b) by 1466 days.

(21) Appl. No.: 12/350,873

(22) Filed: Jan. 8, 2009

(51) Int. Cl.
*A61F 11/00* (2006.01)

(52) U.S. Cl.
USPC .................................. 128/857; 128/858; 2/15

(58) Field of Classification Search
USPC ............. 128/206.13, 206.23, 206.24, 206.27, 128/207.11, 207.17, 857, 858; 2/11, 13, 15, 2/171, 181, 209.13, 195.1, 175.1, 209; 351/45, 46; 602/17; 606/204.15
See application file for complete search history.

(56) References Cited

U.S. PATENT DOCUMENTS

| | | | |
|---|---|---|---|
| 4,411,263 A | 10/1983 | Cook | |
| 4,502,476 A | 3/1985 | Welt | |
| D285,624 S | 9/1986 | Rosenbaum | |
| 4,774,946 A * | 10/1988 | Ackerman et al. | 128/207.18 |
| 5,183,059 A | 2/1993 | Leonardi | |
| 5,521,653 A * | 5/1996 | Anderson | 351/45 |
| 5,613,502 A | 3/1997 | Lee | |
| 5,647,061 A * | 7/1997 | Marcus | 2/11 |
| 5,713,083 A * | 2/1998 | King | 2/416 |
| 6,223,748 B1 | 5/2001 | Chaves et al. | |
| 6,973,930 B2 | 12/2005 | Chilton | |
| 2004/0122344 A1 * | 6/2004 | Nelson et al. | 602/61 |

* cited by examiner

*Primary Examiner* — Michael A. Brown
(74) *Attorney, Agent, or Firm* — Crossley Patent Law; Micah C. Gunn

(57) ABSTRACT

The infant eye guard apparatus has an elasticized lateral band to which is permanently adjoined one end of the elasticized cranial band. The T-member of the cranial band is selectively affixed to the interior of the lateral band posterior. The selectively affixed eye guard is typically worn partially below the lateral band. The cranial band can be worn from anterior to posterior on an infant's head, or side-to-side and the eye guard selectively fitted to the lateral band interior lateral loop. The lateral band is adjustable via elasticizing and also via the cut line by which the lateral band can be divided and adjustably fitted with the T-member of the cranial band. The cranial band prevents any downward slip of the lateral band. The orbitals of the eye guard fully cover and surround the exterior of an infant's eye, thereby ensuring no light invasion.

1 Claim, 5 Drawing Sheets

INFANT EYE GUARD APPARATUS

BACKGROUND OF THE INVENTION

Especially premature but even term babies sometimes need phototherapy for treatment of hyperbilirubinemia (jaundice). Previously designed eye protection devices do not provide optimal comfort, position retention, easy fit and removal, and ensured eye protection. For example, improperly designed devices can slip downwardly on an infant, impinging nose, mouth, or even throat. Not only is this a danger, this is also an interruption in the work schedule of attendants and in phototherapy treatment. The infants must also be protected from any device that may scratch them or cause allergic reaction. Even further, devices which are aggressively elastic or which require otherwise excessive pressure for position retention can cause cranial deformity. The present apparatus provides advantages and solutions to these problems.

FIELD OF THE INVENTION

The infant eye guard apparatus relates to eye protection and more especially to eye protection for infants who are subjected to phototherapy.

SUMMARY OF THE INVENTION

The general purpose of the infant eye guard apparatus, described subsequently in greater detail, is to provide a infant eye guard apparatus which has many novel features that result in an improved infant eye guard apparatus which is not anticipated, rendered obvious, suggested, or even implied by prior art, either alone or in combination thereof.

To attain this, the infant eye guard apparatus has a lateral band to which is permanently adjoined one end of the cranial band. The T-member of the cranial band is selectively affixed to the interior of the lateral band posterior. Both the lateral band and the cranial band are soft elasticized material. The eye guard is selectively fitted, as chosen, and is typically worn slightly below the lateral band. The cranial band can be worn from anterior to posterior on an infant's head. The cranial band can also be worn side-to-side and the eye guard selectively fitted to the lateral band interior lateral loop. The lateral band is adjustable via elasticizing and also via the cut line by which the lateral band can be divided and adjustably fitted with the T-member of the cranial band.

Ideally, the lateral band is worn slightly inferior on the head, with the cranial band preventing any downward slip of the lateral band. The orbitals of the eye guard fully cover and surround the exterior of an infant's eye, thereby ensuring no light invasion. While the most basic embodiment provides permanent attachment of the eye guard, the most complete embodiment provides for adjustable selective attachment of the eye guard, ensuring proper fit to any infant in shielding their eyes. The apparatus is light weight and offers no harsh surfaces which might be unpleasant to an infant.

Thus has been broadly outlined the more important features of the improved infant eye guard apparatus so that the detailed description thereof that follows may be better understood and in order that the present contribution to the art may be better appreciated.

An object of the infant eye guard apparatus is to protect an infant's eyes during phototherapy.

Another object of the infant eye guard apparatus is to ensure position retention of the protection over the infant's eyes.

A further object of the infant eye guard apparatus is to prevent any discomfort for the infant regarding eye protection.

And, an object of the infant eye guard apparatus is to avoid impingement on an infant's nose.

Yet another object of the infant eye guard apparatus is to engage the frontal bone zygomatic process region in retaining the apparatus in desired position on an infant.

And, another object of the infant eye guard apparatus is to engage the occipital region in retaining the apparatus in desired position on an infant.

A further object of the infant eye guard apparatus is to prevent the lateral band of the apparatus from slipping downwardly on the occipital region.

An added object of the infant eye guard apparatus is to be adjustable for fit to different sizes of infants.

Yet another object of the infant eye guard apparatus is to provide adjustment in wear position height on an infant's head.

And, another object of the infant eye guard apparatus is to provide circumferential adjust for proper fit to an infant's head.

Still another object of the infant eye guard apparatus is to provide the apparatus in a plurality of sizes.

These together with additional objects, features and advantages of the improved infant eye guard apparatus will be readily apparent to those of ordinary skill in the art upon reading the following detailed description of presently preferred, but nonetheless illustrative, embodiments of the improved infant eye guard apparatus when taken in conjunction with the accompanying drawings.

In this respect, before explaining the current embodiments of the improved infant eye guard apparatus in detail, it is to be understood that the infant eye guard apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved infant eye guard apparatus. It is therefore important that the claims be regarded as including such equivalent constructions insofar as they do not depart from the spirit and scope of the infant eye guard apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 5 thereof, the principles and concepts of the infant eye guard apparatus generally designated by the reference number 10 will be described.

Figure 5:
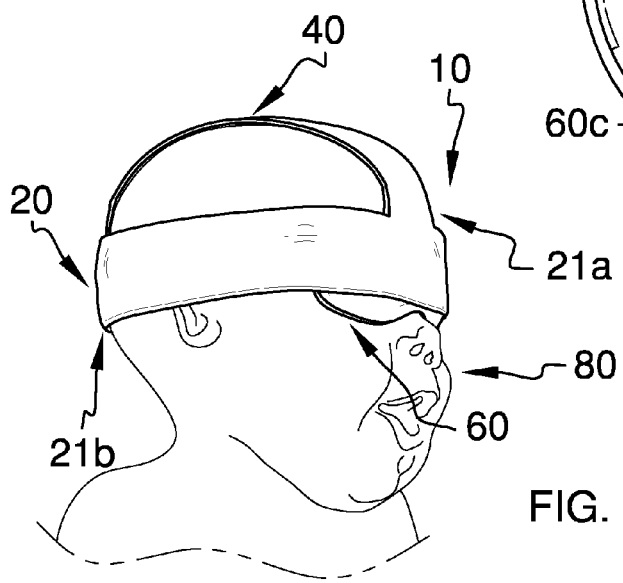
FIG. 5 is a frontal perspective view of the apparatus fitted to an infant.
Figure 6:
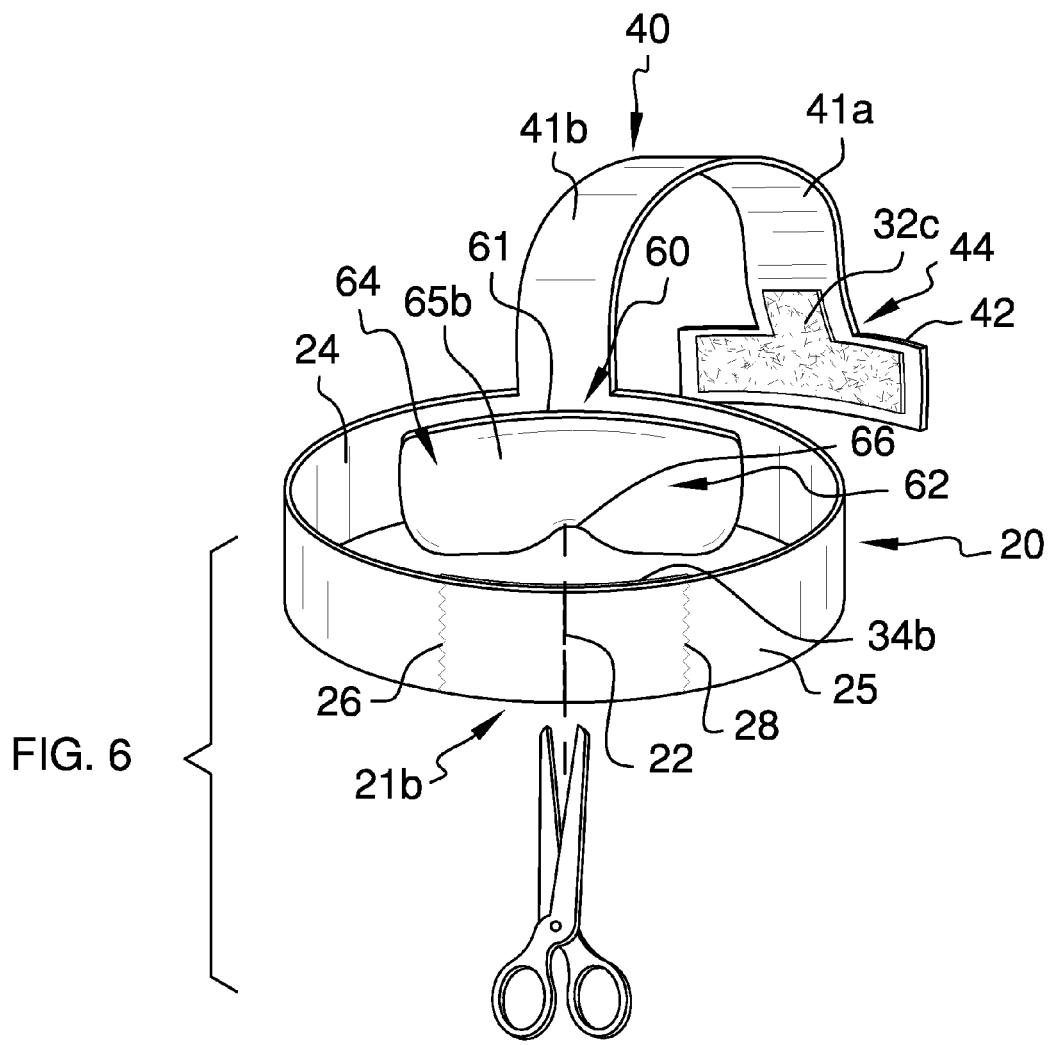
FIG. 6 is a posterior perspective view, cranial band T-member disengaged.
Figure 7:
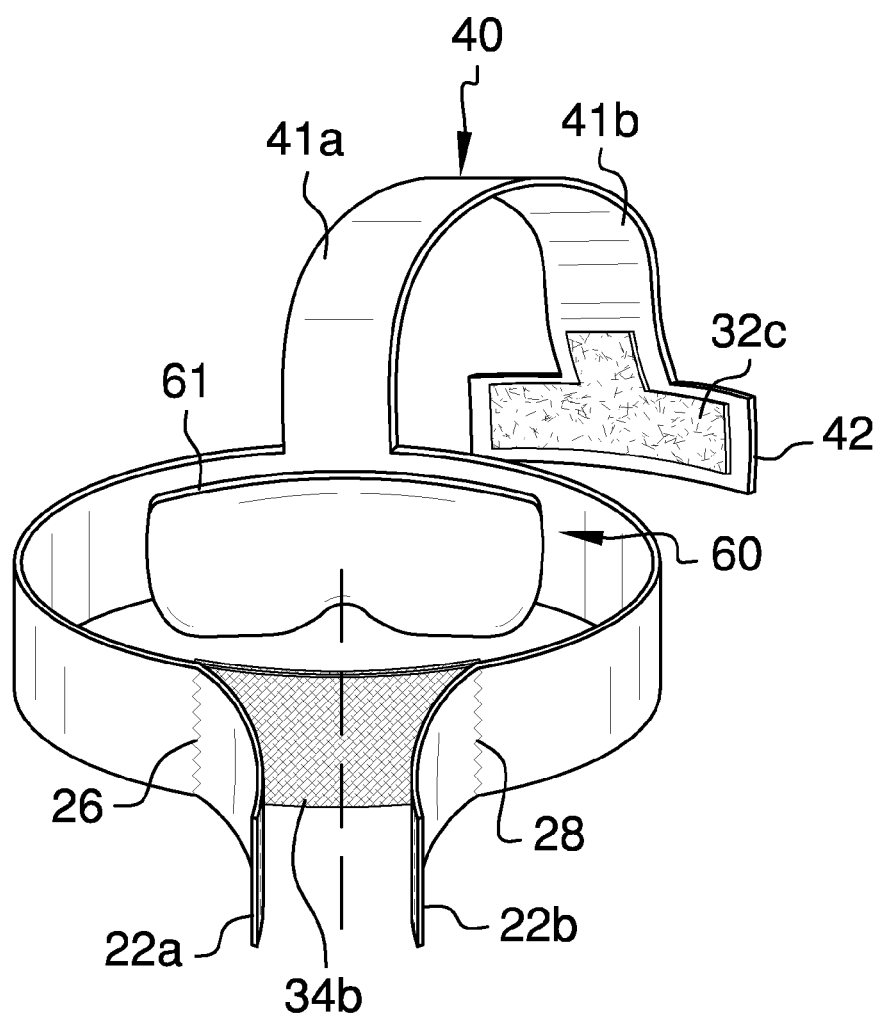
FIG. 7 is a posterior perspective view, lateral band cut.

Referring to FIG. 5, the infant eye guard apparatus 10 removably encircles an infant's 80 head. The anterior 21*a* of the soft elasticized lateral band 20 selectively engages the zygomatic region of the infant's 80 head. The posterior 21*b* of the lateral band 20 selectively engages a slightly inferior occipital region of the infant's 80 head. The soft elasticized cranial band 40 prevents the lateral band 20 from slipping downwardly on the head. The eye guard 60 prevents light invasion of the infant's 80 eyes during phototherapy.

Figure 1:
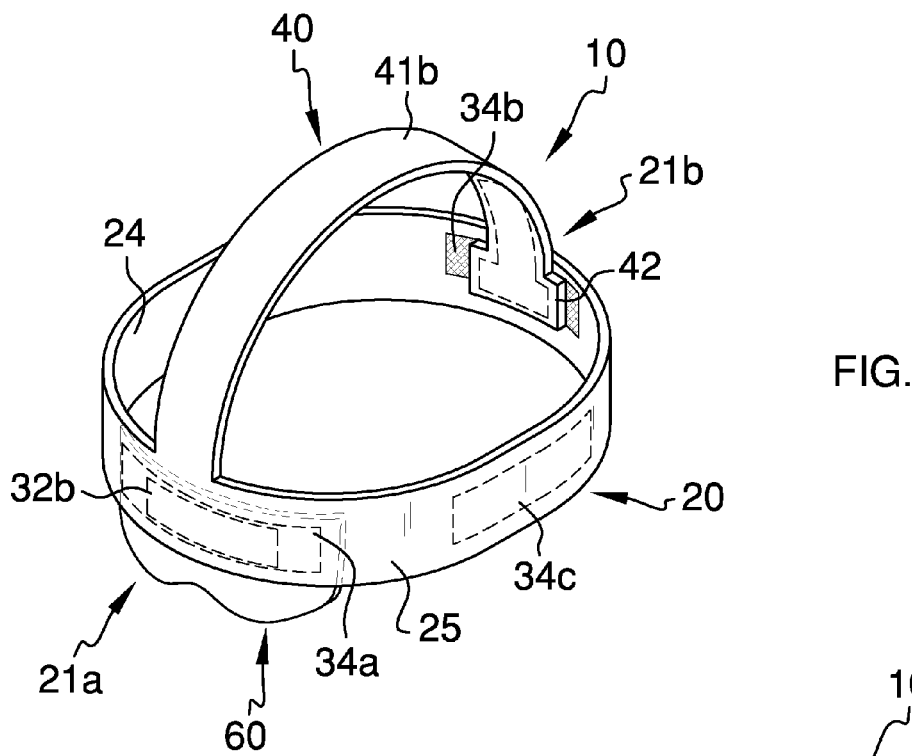
FIG. 1 is an anterior perspective view.
Figure 2:
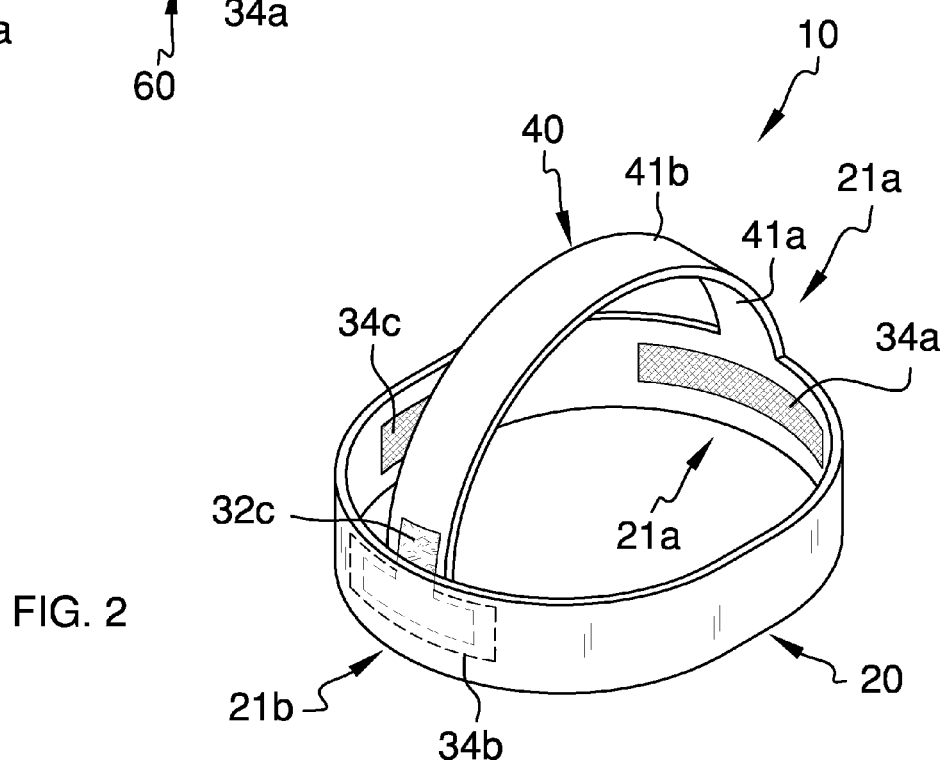
FIG. 2 is a posterior perspective view.
Figure 3:
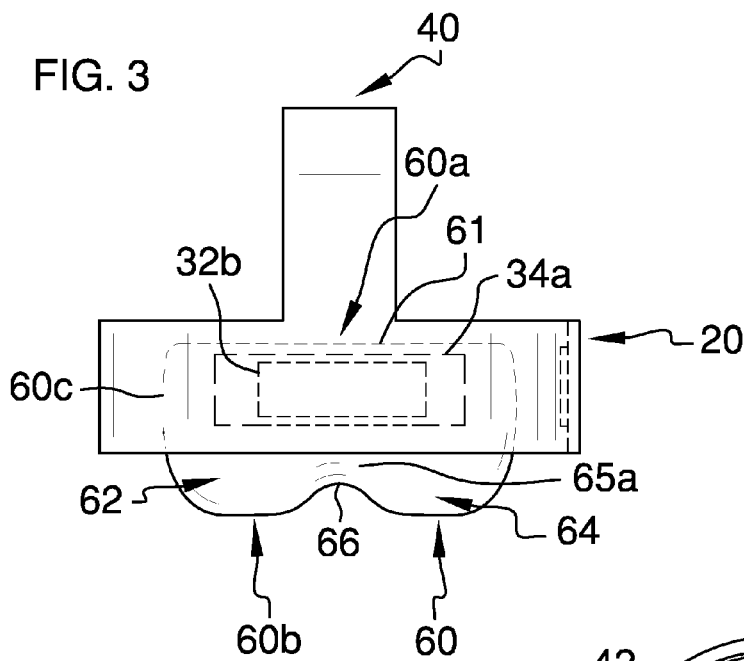
FIG. 3 is a front elevation view.

Referring to FIGS. 1 and 2, the apparatus 10 has an anterior 21*a* spaced apart from a posterior 21*b*. The anterior loop 34*a* of hook and loop is affixed to the anterior 21*a* band interior 24 of the lateral band 20. The posterior loop 34*b* of hook and loop is affixed to the posterior 21*b* band interior 24 of the lateral band 20 by a pair of spaced apart stitches. The stitches comprise the first stitch 26 and the second stitch 28. A lateral loop 34*c* of hook and is loop disposed laterally on the band interior 24 of the lateral band 20. The lateral loop 34*c* is disposed about midway between the anterior loop 34*a* and the posterior loop 34*b*.

Referring to FIGS. 6, 7, 8, and 9, the cut line 22 is defined on the posterior 21*b* lateral band 20. The cut line 22 is disposed midway between the first stitch 26 and the second stitch 28. The cut line 22 selectively guides a cut of the posterior 21*b* lateral band 20. The stitches anchor the ends of the lateral loop 34*c* to the lateral band 20. The cut forms the first cut end 22*a* and the second cut end 22*b*.

Figure 4:
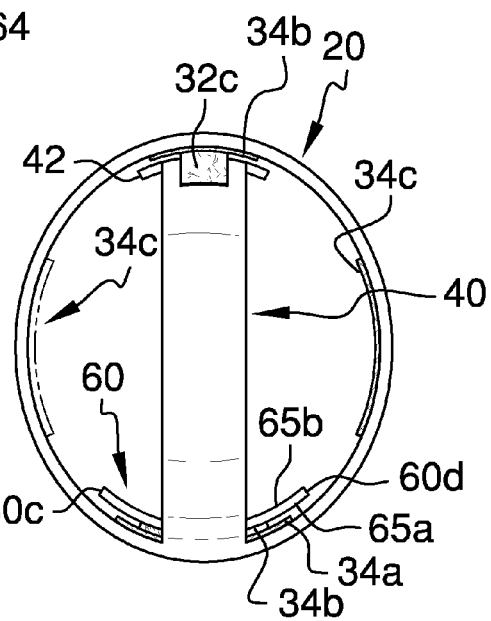
FIG. 4 is a top plan view.
Figure 8:
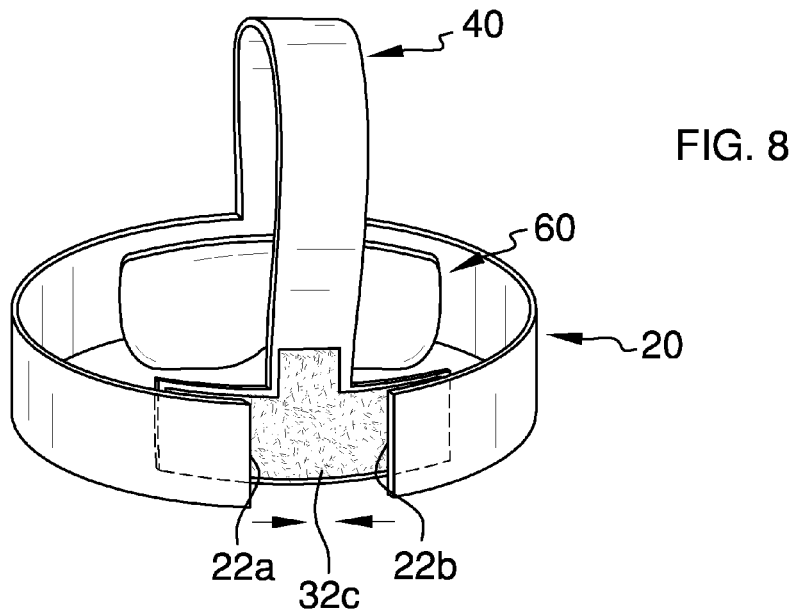
FIG. 8 is a posterior perspective view, the first and second cut ends hooked to the T-member.
Figure 9:
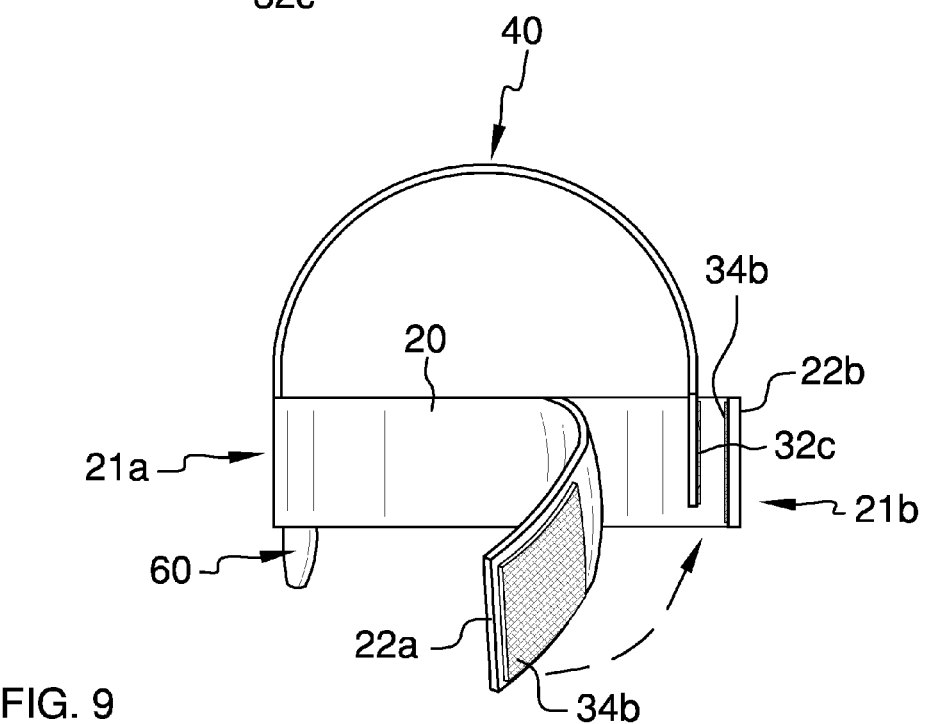
FIG. 9 is a lateral perspective view, the first cut end and the second cut end of the lateral band disengaged from the T-member of the cranial band.

Referring to FIGS. 4 and 8, the elasticized cranial band 40 is affixed perpendicularly to the anterior 21*a* lateral band 20. The cranial band 40 has a soft cranial band interior 41*a* and a soft cranial band exterior 41*b*. The T-member 42 comprises the distal end of the cranial band 40. The T-member 42 is perpendicular to a length of the cranial band 40. T-member hook 32*c* of hook and loop is disposed in the cranial band exterior 41*b* T-member 42.

Referring to FIGS. 2 and 4, the lateral loop 34*c* selectively provides for the apparatus 10 to be worn with the cranial band 40 placed across the head, rather than the cranial band 40 being positioned fore to aft (anterior to posterior) on an infant's 80 head. With the cranial band 40 worn from side to side, the eye guard 60 can be hooked to the lateral loop 34*c*. The lateral loop 34*c* is not relegated to only one side of the band interior 24 of the lateral band 20.

Referring to FIGS. 3, 4, 5, and 6 the eye guard 60 has a first side 65*a* and a second side 65*b*. The guard top 60*a* is spaced apart from the guard bottom 60*b*. The right side 60*c* is spaced apart from the left side 60*d*. The eye guard 60 further comprises the straight upper ridge 61. The right orbital 62 is disposed under the ridge 61 adjacent to the right side 60*c*. The left orbital 64 is disposed under the ridge 61 adjacent to the left side 60*d*.

The concave section 66 is disposed on the guard bottom 60*b* between the right orbital 62 and the left orbital 64. The eye guard hook 32*b* is affixed to the eye guard 60 first side 65*a*. The eye guard hook 32*b* is most proximal to the guard top 60*a*. The eye guard hook 32*b* is selectively affixed to the lateral band 20 anterior loop 34*a*. The eye guard 60 is selectively affixed such that a portion of the orbitals and the concave section 66 extend below the lateral band 20, thus best covering the infant's 80 eyes. As previously noted, the eye guard hook 32*b* is further selectively affixed to the lateral loop 34*c* of the lateral band 20.

With respect to the above description then, it is to be realized that the optimum dimensional relationships for the parts of the infant eye guard apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the infant eye guard apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the infant eye guard apparatus may be used.

Therefore, the foregoing is considered as illustrative only of the principles of the infant eye guard apparatus. Further, since numerous modifications and changes will readily occur to those skilled in the art, it is not desired to limit the infant eye guard apparatus to the exact construction and operation shown and described, and accordingly, all suitable modifications and equivalents may be resorted to, falling within the scope of the infant eye guard apparatus.

What is claimed is:

1. An infant eye guard apparatus comprising:
    an elasticized lateral band selectively and removably configured to encircle an infant's head horizontally, the lateral band having an anterior spaced apart from a posterior, a soft interior and a soft exterior, the anterior configured to selectively engage a zygomatic region of the infant's head, the posterior configured to selectively engage a slightly inferior occipital region of the infant's head;
    an anterior loop of a hook and loop affixed to the anterior band interior of the lateral band;
    a posterior loop of hook and loop affixed to the posterior band interior of the lateral band by a pair of spaced apart stitches, the stitches comprising a first stitch and a second stitch;
    a lateral loop of hook and loop disposed laterally on the band interior of the lateral band, the lateral loop about midway between the anterior loop and the posterior loop;
    a cut line defined on the posterior lateral band, the cut line disposed midway between the first stitch and the second stitch, the cut line selectively guiding a cut of the posterior lateral band, the cut forming a first cut end and a second cut end;
    a soft elasticized cranial band affixed perpendicularly to the anterior lateral band, the cranial band having a soft cranial band interior and a soft cranial band exterior;
    a T-member comprising a distal end of the cranial band, the T-member perpendicular to a length of the cranial band;
    a T-member hook of hook and loop disposed in the T-member cranial band exterior;
    an eye guard having a first side and a second side, a guard top spaced apart from a guard bottom, a right side spaced apart from a left side, the eye guard further comprising:
        a straight upper ridge;
        a right orbital disposed under the ridge adjacent to the right side;
        a left orbital disposed under the ridge adjacent to the left side;
        a concave section disposed on the guard bottom between the right orbital and the left orbital;
    an eye guard hook affixed to the eye guard first side, the eye guard hook most proximal to the eye guard top, the eye guard hook selectively affixed to the lateral band anterior loop, wherein only a portion of the orbitals and only a portion of the concave section extend below the lateral band;

wherein the eye guard hook is alternately affixed to the lateral loop of the lateral band.

* * * * *